(12) United States Patent
Kelly et al.

(10) Patent No.: US 9,579,105 B2
(45) Date of Patent: Feb. 28, 2017

(54) SAGITTAL SAW

(75) Inventors: Matthew P. Kelly, Ithaca, NY (US);
Timothy B. Lannin, Ithaca, NY (US);
Thomas P. James, Boxford, MA (US)

(73) Assignee: TUFTS UNIVERSITY, Medford, MA (US)

( * ) Notice: Subject to any disclaimer, the term of this patent is extended or adjusted under 35 U.S.C. 154(b) by 368 days.

(21) Appl. No.: 14/125,164

(22) PCT Filed: Jun. 6, 2012

(86) PCT No.: PCT/US2012/040986
§ 371 (c)(1),
(2), (4) Date: May 13, 2014

(87) PCT Pub. No.: WO2012/170459
PCT Pub. Date: Dec. 13, 2012

(65) Prior Publication Data
US 2014/0243832 A1 Aug. 28, 2014

Related U.S. Application Data

(60) Provisional application No. 61/495,678, filed on Jun. 10, 2011.

(51) Int. Cl.
*A61B 17/14* (2006.01)
(52) U.S. Cl.
CPC ............ *A61B 17/148* (2013.01); *A61B 17/14* (2013.01)

(58) Field of Classification Search
CPC ............ A61B 17/148; A61B 17/32002; B23D 49/165
See application file for complete search history.

(56) References Cited

U.S. PATENT DOCUMENTS

| 5,439,472 A | 8/1995 | Evans et al. |
| 9,232,949 B2 * | 1/2016 | Carusillo ............... A61B 17/14 |
| 2006/0009796 A1 | 1/2006 | Carusillo et al. |
| 2007/0016238 A1 | 1/2007 | Marietta |
| 2008/0027449 A1 | 1/2008 | Gundlapalli et al. |
| 2010/0228256 A1 | 9/2010 | Walen et al. |

* cited by examiner

*Primary Examiner* — Andrew Yang
(74) *Attorney, Agent, or Firm* — Occhiuti & Rohlicek LLP

(57) ABSTRACT

A sagittal saw includes a blade and an actuator configured to drive the blade. The blade includes a first end, a second end opposed to the first end, and a longitudinal axis extending between the first end and second end. The blade first end extends transverse to the longitudinal axis, and its movement defines a blade path. The blade path comprises a closed plane curve consisting of two loops meeting at a node ie, a figure-eight, whereby the blade path crosses over itself. The actuator includes a gear assembly configured to cyclically drive the blade so that the blade path includes multiple impulsive thrusts along the longitudinal axis in each blade path cycle. In addition, the blade cuts the work piece in both a first direction and a second direction in each blade cycle, the second direction opposed to the first direction.

36 Claims, 9 Drawing Sheets

SAGITTAL SAW

CROSS REFERENCE TO RELATED APPLICATIONS

This application is a National Stage of International Application No. PCT/US2012/040986 filed on Jun. 6, 2012, which claims priority to U.S. Provisional Application No. 61/495,678, filed Jun. 10, 2011, the contents of which are hereby incorporated in their entirety.

BACKGROUND OF THE INVENTION

Sagittal bone saws function through angular oscillation of the saw cutting blade, and are used primarily in applications that require plunge cutting of bone. However, when used at a high cutting rate, sagittal saws can sometimes generate a significant amount of heat, damaging or destroying bone cells in the immediate area of the cut. Damage to bone cells is undesirable since it can delay patient recovery time and reduce the effectiveness of the surgical procedure. One alternative to high cutting rates includes application of an impulsive thrust force wherein the cutting blade includes motion normal to, and directed into, the bone surface.

SUMMARY

In some aspects, a cutting device is provided that includes a blade including a first end, a second end opposed to the first end, and a longitudinal axis extending between the first end and second end. The first end extends transverse to the longitudinal axis, and movement of the first end defines a blade path. The device also includes an actuator connected to the blade second end. The actuator is configured to drive the blade so that the blade path comprises a cyclic closed planer loop that crosses over itself at least once per blade path cycle.

In some aspects, a cutting device is provided that includes a blade including a first end, a second end opposed to the first end, and a longitudinal axis extending between the first end and second end. The first end extends transverse to the longitudinal axis, and movement of the first end defines a blade path. The device also includes an actuator connected to the blade second end. The actuator is configured to drive the blade so that the blade path is cyclic and includes at least two reciprocations parallel to the longitudinal axis for each blade path cycle.

The cutting device may include one or more of the following features: In one blade path cycle, the blade path comprises a closed plane loop consisting of at least two lobes meeting at a node. The lobes are symmetric. The lobes are asymmetric. The blade path is symmetric about an axis parallel to the longitudinal axis. A portion of the blade path corresponding to a first reciprocation of the at least two reciprocations is a different portion than a portion of the blade path corresponding to a second reciprocation of the at least two reciprocations. The blade moves along the blade path in such a way that a workpiece is cut both in a first direction and a second direction, the second direction being opposed to the first direction. The first direction and second direction are generally transverse to the blade longitudinal axis. The movement in the second direction is subsequent to movement in the first direction. The blade cuts the work piece in both the first direction and a second direction within the same blade path cycle. In one blade path cycle, the blade moves along the blade path in such a way that a work piece is cut both in a first direction and a second direction, the second direction being opposed to the first direction, wherein the portion of the blade path corresponding to movement in the first direction is a different portion than the portion of the blade path corresponding to movement in the second direction. The blade path crosses over itself at least once per blade cycle.

The cutting device may include one or more of the following additional features: The actuator comprises a gear assembly configured to be driven by a motor. The gear assembly includes a thrust shaft driven by the motor, the thrust shaft including an end and a thrust crank protruding from the thrust shaft end so as to extend parallel to and spaced apart from an axial centerline of the thrust shaft. The gear assembly includes a first gear mounted on the thrust shaft. The gear assembly includes a cutting shaft parallel to the thrust shaft, the cutting shaft including an end and a cutting crank protruding from the cutting shaft end so as to extend parallel to and spaced apart from an axial centerline of the cutting shaft. The gear assembly includes a second gear mounted on the cutting shaft and driven by the first gear, and a pivot shaft parallel to the cutting shaft. The first and second gears are dimensioned so that the rotational speed of the thrust shaft is greater than the rotational speed of the cutting shaft. The first and second gears are dimensioned so that the rotational speed of the thrust shaft is an integer multiple of the rotational speed of the cutting shaft. The first and second gears are dimensioned so that the rotational speed of the thrust shaft is at least twice the rotational speed of the cutting shaft. The cutting crank is connected to the blade using a first guide configured to convert the rotary motion of the cutting crank to a linear motion of the blade that is transverse to the longitudinal axis. The thrust crank is connected to the blade at a location between the first guide and the first end using a second guide, the second guide configured to convert the rotary motion of the thrust crank to a linear motion of the blade that is parallel to the longitudinal axis, and the pivot shaft is connected to the blade at a location between the second guide and the first end using a third guide, the third guide configured to constrain the longitudinal axis of the blade to intersect with a longitudinal axis of the pivot shaft. The first guide, second guide and third guide are linear guide bearings. The cutting crank and the thrust crank are arranged so that an initial phase difference exists between the cutting crank angular position and the thrust crank angular position. The cutting crank and the thrust crank are arranged so that the initial phase difference between the cutting crank angular position and the thrust crank angular position is greater than 0 degrees and less than 90 degrees. The cutting crank and the thrust crank are arranged so that the initial phase difference between the cutting crank angular position and the thrust crank angular position is greater than 90 degrees and less than 180 degrees.

Advantageously, a sagittal saw is provided that achieves increased cutting rates, whereby overall cutting times are reduced, with corresponding reductions in patient time spent with a limb under tourniquet, as required in some surgical procedures such as knee replacement. One reason for increased cutting rates is due to dynamically applied thrust forces generated within the saw assembly.

Further advantageously, the sagittal saw includes a gear assembly driven by the motor and connected to the saw blade. The gear assembly is configured to cyclically drive the cutting blade so that the blade cutting edge travels along a closed, planar, multi-lobed loop in each cycle of motion. For example, for a particular gear configuration, the blade cutting edge travels along a generally figure-eight shaped path. As such, the blade cutting edge experiences two thrusts (movements parallel to the blade longitudinal axis, and in a direction normal to a surface of the bone and toward the bone interior) for each blade cycle. Additional thrusts per blade cycle can be obtained by a simple change of the gear ratio.

The sagittal saw provides a dynamically-applied thrust force along an axial direction of the saw blade, yielding a larger depth of cut by the saw blade, resulting in more efficient cutting. Moreover, since the saw itself provides the thrust force, as compared to a static thrust manually applied to the tool by the user, a larger thrust force is applied to the work piece surface than can be manually applied by the user. Still further, the user has better control of the cut when achieved using the dynamically-applied thrust.

The gear assembly is configured to drive the cutting blade in a cutting motion that includes movements transverse to the blade longitudinal axis, and in a direct parallel to a surface of the bone. Advantageously, the blade path cuts the work piece in opposing directions, first in one direction during the first blade thrust, and then in the opposed direction during the second blade thrust. Thus, the cutting blade cuts the bone surface twice in each blade cycle. This feature provides a cutting tool that is easier and more comfortable to use than a conventional sagittal saw, which in some cases includes an elliptical cutting path that cuts in a single direction, once per blade cycle.

By providing the blade path that is a loop including multiple lobes such as the two-lobed figure-eight blade path, which permits alternation of the direction of the cutting force, the average moment generated by the saw on the handle is zero, which allows the saw to be easily controlled. This feature overcomes a known disadvantage of some conventional, elliptically orbiting sagittal saws, in which a cutting force is always applied in the same direction. While this is effective in linear reciprocating saws and jigsaws, an elliptical orbit can cause a loss of control in a sagittal saw. This is because in a linear saw the cutting force is directed along the length of the blade into the handle, where as in a sagittal saw, the cutting force is directed perpendicular to the length of the blade, creating a net moment on the handle.

Modes for carrying out the present invention are explained below by reference to an embodiment of the present invention shown in the attached drawings. The above-mentioned object, other objects, characteristics and advantages of the present invention will become apparent from the detailed description of the embodiment of the invention presented below in conjunction with the attached drawings.

DETAILED DESCRIPTION

Figure 1:
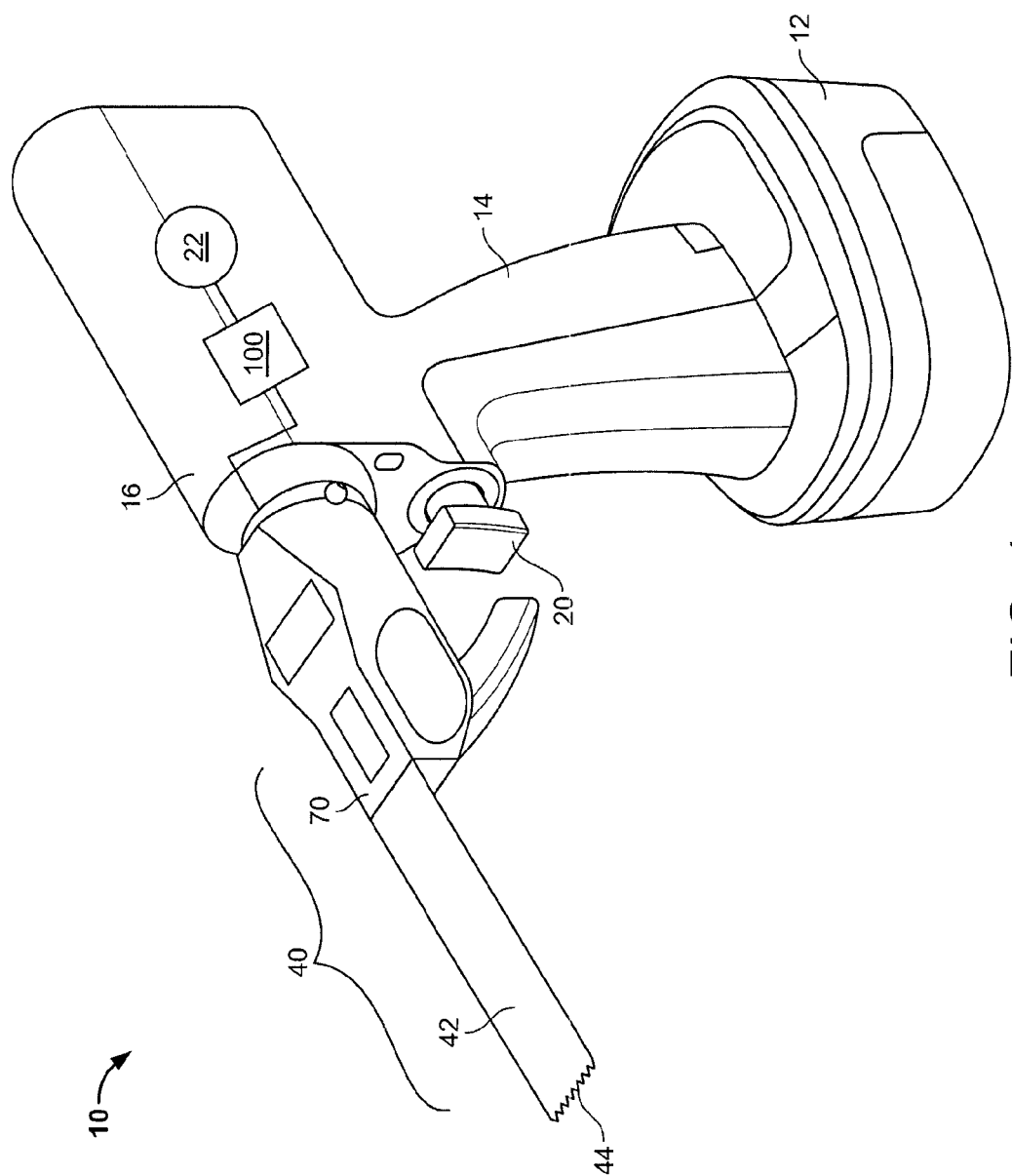
FIG. 1 is a side perspective view of a hand-held, battery-powered sagittal saw.

Referring now to FIGS. 1-4, the sagittal saw 10 is a hand-held device that includes a motor housing 16 and a handle 14 extending from an end of the housing 16. In this embodiment, a battery pack 12 is detachably secured to an end of the handle 14 and serves as a power source for a motor 22 disposed within the housing 16. A gear assembly 100 is also disposed within the housing 16 and connects the motor 22 to a blade assembly 40. The gear assembly 100 is driven by the motor 22, and in turn drives the blade assembly 40 in such a way as to increase cutting speed and reduce heat generation by the saw 10 as compared to some conventional sagittal saws. As discussed further below, a cutting edge 44 of a saw blade 42 is driven by the gear assembly 100 along a planar cyclic path that is generally in the form of a figure-eight, or, in other words, a closed planar loop curve consisting of two lobes meeting at a node. The lobes may be symmetric or asymmetric.

The cyclic figure-eight motion of the blade 42 permits the blade cutting edge 44 to impart two thrusts for each blade cycle. Here, a thrust force is defined as a component of the force generated by the saw that is applied in a direction parallel to the blade longitudinal axis 48 and away from a handle 14 of the saw 10. When the saw 10 is in use cutting a bone 2, the thrust force is applied in a direction normal to a surface 4 of the bone 2 and toward the bone interior.

In addition, the cyclic, figure-eight motion of the blade 42 permits the cutting edge 44 to cut the work piece (e.g., bone) twice in each blade cycle. Here, a cutting force is defined as a component of the force generated by the saw 10 that is applied in a direction transverse to the blade longitudinal axis 48. In particular, the cutting force is applied to the bone surface in opposed directions that are transverse to the blade longitudinal axis 48, first in one direction, and subsequently in the other direction during a single blade cycle. When the saw 10 is in use cutting a bone 2, each of the opposed cutting forces are applied in a direction parallel to a surface 4 of the bone 2. Moreover, a cutting force is applied at the same time as a thrust force.

Figure 2:
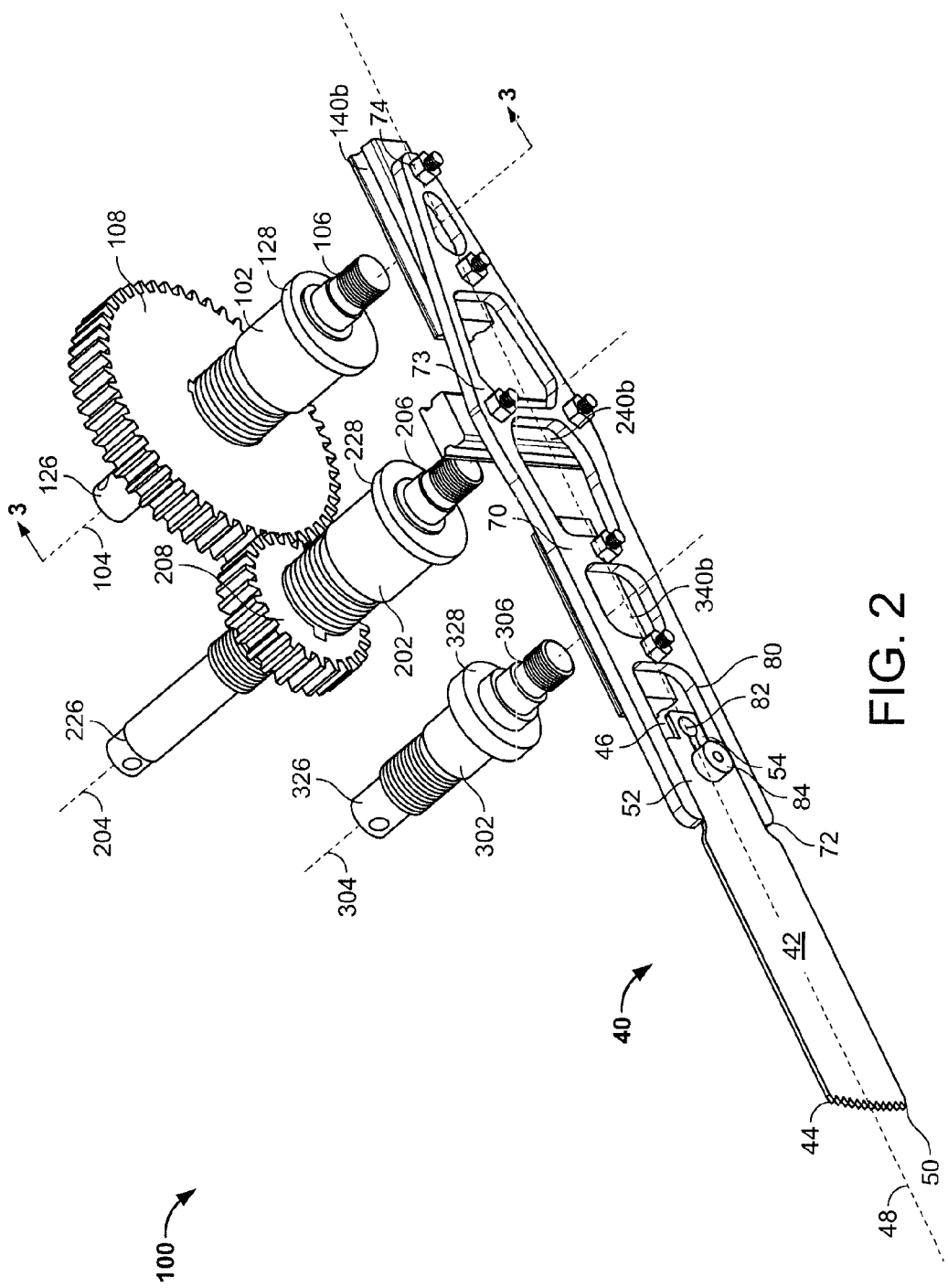
FIG. 2 is a perspective view of the blade assembly and the gear assembly of the saw of FIG. 1, the gear assembly shown without support structure to improve clarity.

Referring to FIG. 2, the blade assembly 40 includes a saw blade 42 supported on a blade holder 70. The saw blade 42 includes the first end 44, a second end 46 opposed to the first end 44, and the longitudinal axis 48 that extends between the first end 44 and the second end 46. In the illustrated embodiment, the first end 44 is generally linear in shape, extends transverse to the longitudinal axis 48, and defines the blade cutting edge. The first end 44 includes several cutting teeth 50 protruding generally parallel to the longitudinal axis. The teeth 50 are configured to cut bone, and in some embodiments may include features (not shown) to enhance cutting such as a particular tooth shape, spacing and/or set.

The blade second end 46 is shaped to facilitate secure connection to the blade holder 70. In the illustrated embodiment, the second end 46 includes a reduced-width neck portion 52 dimensioned to be received within a corresponding channel 80 formed in the blade holder 70, as discussed further below. The neck portion 52 includes a through-thickness slot 54 that opens at the blade second end 46. The slot 52 intersects two openings 56, 58 formed in the neck portion to receive fasteners such as a pin 82 and bolt 84, which are used to retain the blade 42 within the blade holder 70.

The blade 42 is thin relative to its width and axial length, and the axial length is much greater than the width. In the illustrated embodiment, the blade 42 has an axial length of 86.7 mm, a width of 24.8 mm and a thickness of 1.22 mm. For example, the blade 42 may be a model 2108-210 sagittal saw blade manufactured by Stryker Corporation of Kalamazoo, Mich., U.S.A. These dimensions are provided to illustrate the relative scale of the blade 42, and are not intended to be limiting. It is understood that overall blade and tooth shape, configuration, and size can vary and are determined by the specific requirements of the application.

The blade holder 70 is used to connect the blade 42 to the gear assembly 100. This connection occurs through a bearing assembly, as described further below. The blade holder 70 is an elongated plate having a first end 72, and a second end 74 opposed to the first end. The blade holder first end 72 is configured to receive and retain the blade second end 46. To that effect, the blade holder first end 72 includes the blade-receiving channel 80, which is formed in a side surface of the blade holder 70 and extends axially inward from the first end 72. The channel 80 has a width corresponding to the width of the blade neck portion 52, and includes fasteners for retaining the blade neck portion 52 within the channel 80. For example, in the illustrated embodiment, a pin 82 protrudes from a surface of the channel 80 and is received within the corresponding opening 58 (shown in FIG. 7) of the blade second end 46. In addition, a bolt 84 extends through the other blade opening 56 (shown in FIG. 7) and through a corresponding through hole (not shown) formed in the blade holder 70. The channel 80, pin 82 and bolt 84 securely fix the blade 42 to the holder 70.

The blade holder 70 supports three linear guide bearings 140, 240, 340 (only the rail portions 140b, 240b, 340b of the linear guide bearings are shown). As discussed further below, the linear guide bearings 140, 240, and 340 serve as connections between the blade holder 70 and the respective output shafts 102, 202 and stationary shaft 302 of the gear assembly 100, and are located at spaced locations between the blade holder first end 72 and second end 74.

Figure 3:
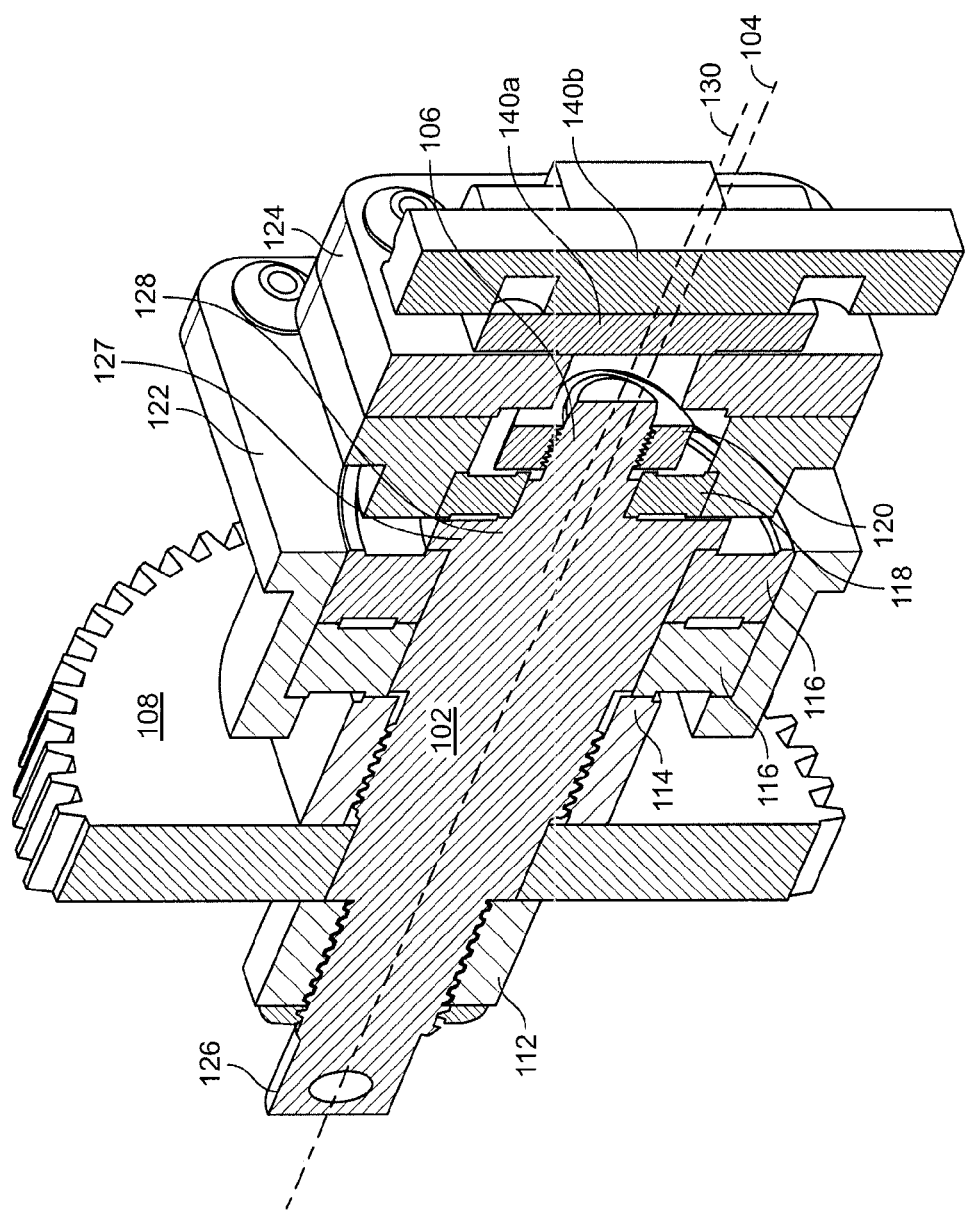
FIG. 3 is a perspective cross-sectional view of a portion the gear assembly of the saw of FIG. 1 as seen along line 3-3 of FIG. 2.

Referring to FIG. 3, the gear assembly 100 includes a cutting shaft 102 including a cutting shaft axis 104 that is arranged to extend transverse to, and intersect, the blade longitudinal axis 48 at a location adjacent the second end 74 of the blade holder 70. The cutting shaft 102 is rotatably supported within the motor housing 16 by bearings 116, which in turn are housed within a fixed bearing housing 122 that is fixed to the motor housing 16. The cutting shaft 102 and bearings are retained in this configuration using a nut 114 that secures the cutting shaft 102 relative to an annular flange 127 formed on the shaft second end 128. A cutting gear 108 is disposed on the cutting shaft 102 adjacent to a shaft first end 126, and is retained at this location using a second nut 112. A cutting crank 106 protrudes from the end face of the cutting shaft second end 128. The cutting crank 106 includes a crank axis 130 that is arranged to extend parallel to, and radially offset from, the cutting shaft axis 104. The cutting crank 106 supports a second bearing 118 and movable hearing housing 124 such that the movable bearing housing 124 follows the circular motion of the crank axis 130 about the cutting shaft axis 104. The movable hearing housing 124 is connected to the cutting shaft linear guide bearing 140.

The cutting shaft linear guide bearing 140 is disposed adjacent the second end 74 of the blade holder 70 and includes a first portion 140a that is fixed to the movable bearing housing 124, and a second portion (e.g, rail portion) 140b that is fixed to the blade holder 70 and moves linearly. The cutting shaft linear guide bearing 140 is oriented so that the second portion 140b limits the circular movement of the movable bearing housing 124, and thus the cutting crank 106, relative to the blade holder 70 to movement along the longitudinal axis 48 of the blade 42. As a result, since the cutting shaft linear guide bearing 140 permits movement of the cutting crank 106 only along the blade longitudinal axis 48, the blade holder second end 74 is caused to reciprocate in a direction that is transverse to the blade longitudinal axis 48 and parallel to the blade first end (e.g., cutting edge) 44.

Figure 5:
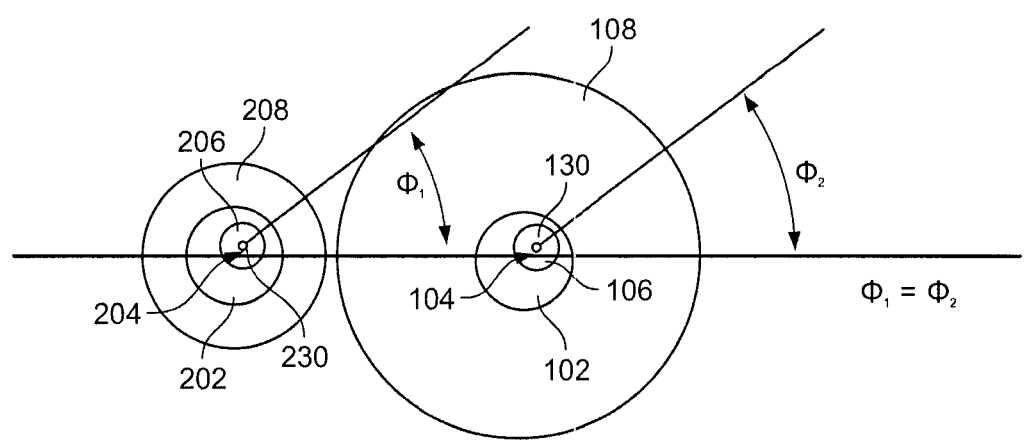
FIG. 5 is an end view of the drive shaft and thrust shaft of FIG. 2 illustrating the cutting crank and the thrust crank arranged so that a 0 degree phase difference exists between the cutting crank angular position and the thrust crank angular position.
Figure 6:
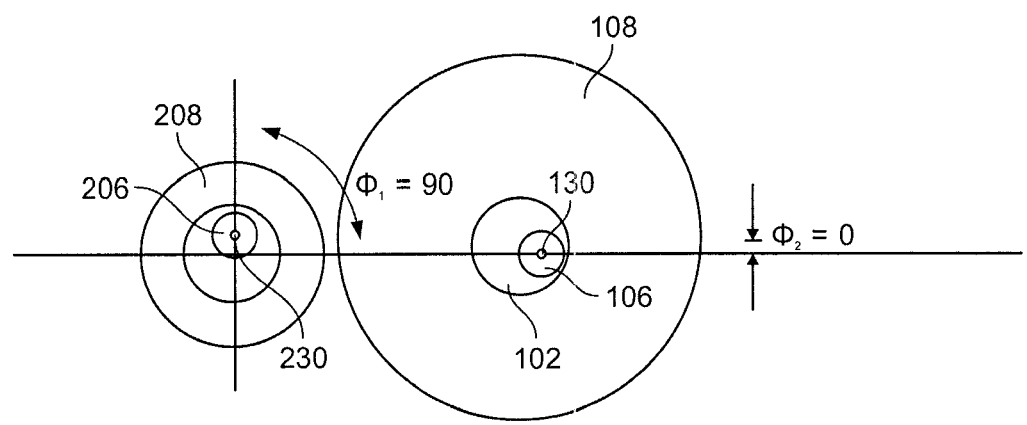
FIG. 6 is an end view of the drive shaft and thrust shaft of FIG. 2 illustrating the cutting crank and the thrust crank arranged so that a 90 degree phase offset (e.g., phase difference) exists between the cutting crank angular position and the thrust crank angular position.

Referring again to FIG. 2, the gear assembly 100 also includes a thrust shaft 202 including a thrust shaft axis 204 that is arranged to extend parallel to the cutting shaft axis 104. In addition, the thrust shaft axis 204 extends transverse to and intersects the blade longitudinal axis 48 at a location generally mid way between the blade holder first end 72 and blade holder second end 74. A thrust gear 208 is disposed on the thrust shaft 202 between the thrust shaft's first and second ends 226, 228. The thrust shaft 202 is supported within the saw housing 16 in a manner similar to that of the cutting shaft 102. Due to similarities in the support structure, the support structure details are not repeated here. A thrust crank 206 protrudes from the end face of the thrust shaft second end 228. The thrust crank 206 includes a crank axis 230 (shown in FIGS. 5 and 6) that is arranged to extend parallel to, and radially offset from, the thrust shaft axis 204. The thrust crank 206 supports a bearing (not shown) and movable hearing housing (not shown) such that the movable bearing housing follows the circular motion of the thrust crank axis about the thrust shaft axis 204. The thrust crank movable hearing housing is connected to the thrust shaft linear guide bearing 240.

The thrust shaft linear guide bearing 240 is disposed generally mid way between the blade holder first end 72 and blade holder second end 74, and includes a first portion (not shown) that is fixed to the thrust shaft movable bearing housing, and a second portion 240b that is fixed to the blade holder 70 and moves linearly. The thrust shaft linear guide bearing 240 is oriented to limit movement of the thrust crank 206 relative to the blade holder 70 to movement along a direction transverse to the longitudinal axis 48 of the blade 42. In addition, as the thrust shaft 202 rotates, due to the offset position of the thrust crank 206 relative to the thrust shaft axis 204, the thrust crank 206 and its movable bearing housing move along a circular path as viewed facing an end of the thrust shaft 202. As a result, since the thrust shaft linear guide bearing 240 permits movement of the thrust crank 206 only along a direction transverse to the blade longitudinal axis 48, the blade holder mid portion 73 is caused to reciprocate in a direction that is parallel to the blade longitudinal axis 48 and transverse to the blade first end (e.g., cutting edge) 44.

The thrust shaft 202 and thrust gear 208 are arranged so that the thrust gear 208 engages the cutting gear 108. In some embodiments, the thrust shaft first end 226 is coupled to the motor 22, so that thrust gear 208 drives the cutting gear 108. In the illustrated embodiment, the diameter of the thrust gear 208 is half the diameter of the cutting gear 108. As a result, the rotational speed of the thrust shaft 202 is twice that of the cutting shaft 102.

The gear assembly 100 also includes a pivot shaft 302 including a pivot shaft axis 304 that is arranged to extend parallel to the cutting shaft axis 104. In addition, the pivot shaft 302 is fixed within the saw housing 16 so that the pivot shaft axis 304 extends transverse to and intersects the blade longitudinal axis 48 at a location generally adjacent to the first end 72 of the blade holder 70. A pivot crank 306 protrudes from the end face of the pivot shaft second end 328, and is connected to the pivot shaft linear guide bearing 340 via a bearing (not shown) and movable bearing housing (not shown) in the same manner as the cutting crank 106 described above. The pivot shaft linear guide bearing 340 is disposed adjacent the first end 72 of the blade holder 70 and is oriented to limit movement of the pivot crank 306 relative to the blade holder 70 to movement along the longitudinal axis 48 of the blade 42. In this case, since the pivot shaft 302 is not driven by the motor 22, the pivot crank 306 is stationary. As a result, the pivot shaft linear guide bearing 340 permits movement of the blade holder 70 only along the blade longitudinal axis 48, whereby the pivot shaft 302 serves as pivot point about which the blade holder 70 rotates due to the oscillations generated by the cutting shaft 102. By constraining the transverse motions at the pivot shaft linear guide bearing 340, the linear motion produced by the cutting shaft 102 is converted to an angular motion of the blade holder 70, and thus the blade 42.

Figure 4:
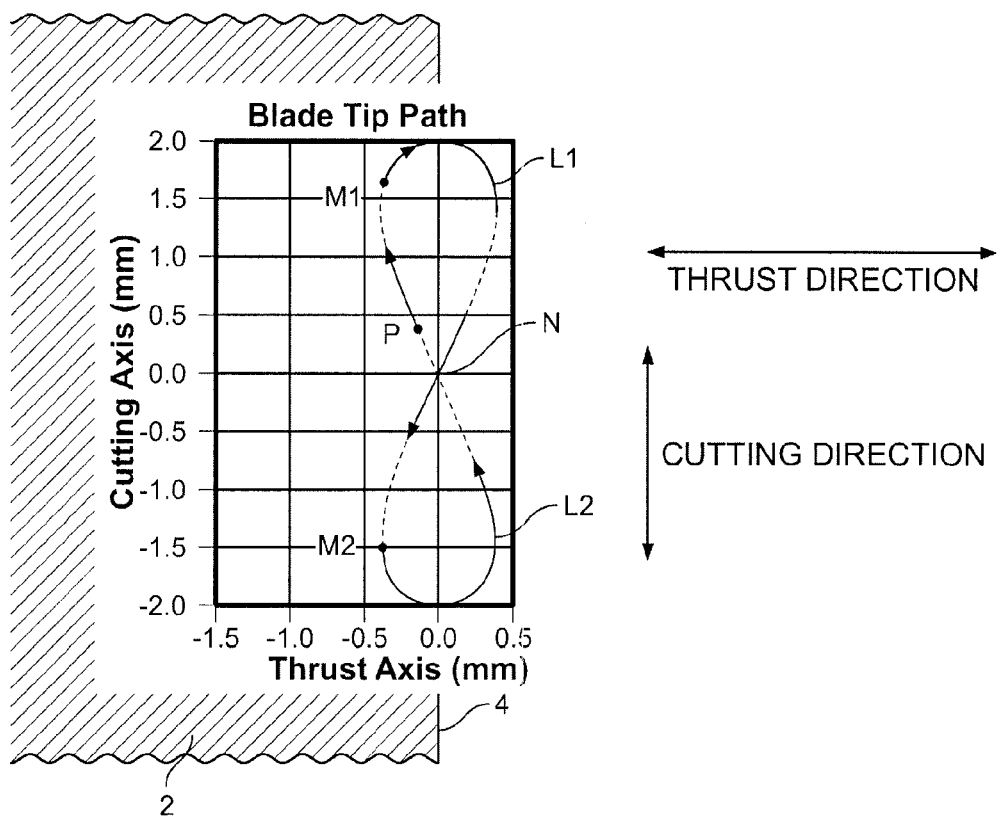
FIG. 4 is a schematic diagram illustrating the path of travel of the cutting edge of the saw blade of FIG. 1.

Referring to FIG. 4, the arrangement of the blade assembly 40 and gear assembly 100 described above provides a sagittal saw 10 in which the cutting edge 44 of the saw blade 42 moves cyclically along a blade path that is a closed plane curve consisting of two lobes L1, L2 meeting at a node N. A figure-eight is an example of a closed plane curve consisting of two lobes meeting at a node in which the two lobes are symmetric. The blade path of the sagittal saw 10, however, is not limited to a path in which the two lobes are symmetric. In addition, it is understood that the blade path includes movement along the curve in such a way that the blade path crosses over itself. For example, assuming the blade path begins at a point P on the first lobe L1, the path follows the first lobe L1 to the node N, crosses the node N to the second lobe L2, moves along the second lobe L2 until it reaches the node N again, and crosses the node N for a second time to return to the first lobe L1, completing a cycle when it reaches the point P.

In the example of the figure-eight shaped blade path shown in FIG. 4, the node N is configured to be at the center of the figure, and a first cutting stroke begins at the node N and moves in the positive cutting direction and generally transverse to the bone surface 4. A first thrust is performed coincidentally with the first cutting stroke, with a maximum thrust amplitude being achieved at point M1. The blade 42 is then slightly withdrawn from the bone 2 as the blade path moves long the right hand side of the first lobe L1. After crossing the node N, a second cutting stroke begins at the node N and moves in the negative cutting direction and generally transverse to the bone surface 4. A second thrust is performed coincidentally with the second cutting stroke, with another maximum thrust amplitude being achieved at point M2. The blade 42 is then slightly withdrawn from the bone 2 as the blade path moves long the right hand side of the second lobe L2 and back to the node N.

Thus, for each cycle of the blade path, the blade path includes two reciprocations parallel to the longitudinal axis for each reciprocation transverse to the longitudinal axis. The second reciprocation occurs subsequent to the first reciprocation, and occurs over a portion of the blade path that is different than that of the first reciprocation. In addition, the blade 42 cuts the work piece in both a first direction and a second direction within the same cycle, where the first and second directions are opposed, and generally transverse to the blade longitudinal axis 48. The movement in the second direction is subsequent to the movement in the first direction, and occurs over a portion of the blade path that is different than that of the first direction.

When all other parameters were held constant, the addition of an impulsive force at the start of each cut had the effect of increasing the cutting rate by an average factor of 2.2. In general, the sagittal saw including the figure eight blade path roughly doubled the cutting rate when compared to some conventional bone saws under otherwise same conditions.

The blade path is based on the geometry of the gear assembly 100 and blade assembly 40 described above, including the radial offset of the cutting shaft crank 106 from the cutting axis 104, the radial offset of the thrust shaft crank 206 from the thrust axis 204, the distance between the thrust shaft 202 and the pivot shaft 302, the distance between the thrust shaft 202 and the cutting shaft 102, and the gear ratio of the cutting gear 108 and the thrust gear 208.

Referring also to FIGS. 5-9, the overall shape of the blade path can be adjusted, for example, by controlling the phase difference between the cutting shaft crank 106 and the thrust shaft crank 206. For example, in the illustrated embodiment including a gear ratio of 2:1, if the phase angle $\Phi 1$ of the thrust crank 206 is initially set equal to the phase angle $\Phi 2$ of the cutting crank 106 (FIG. 5), the blade path is an open curve (see FIG. 8, BI). Similarly, if the phase angle $\Phi 1$ of the thrust crank 206 is initially set at 90 degrees relative to the phase angle $\Phi 2$ of the cutting crank 106 (FIG. 6), the blade path is an open curve, opening in a direction opposed to that obtained for a zero degree phase difference (see FIG. 9, BV). However, if the phase difference between the phase angle $\Phi 1$ of the thrust crank 206 and the phase angle $\Phi 2$ of the cutting crank 106 is between 0 degrees and 90 degrees and between 90 degrees and 180 degrees, the blade path is a closed plane curve consisting of two lobes meeting at a node. Depending on the specific phase difference, the lobes may be symmetric or asymmetric about axes extending in the cutting direction and/or in the thrust direction.

Figure 7:
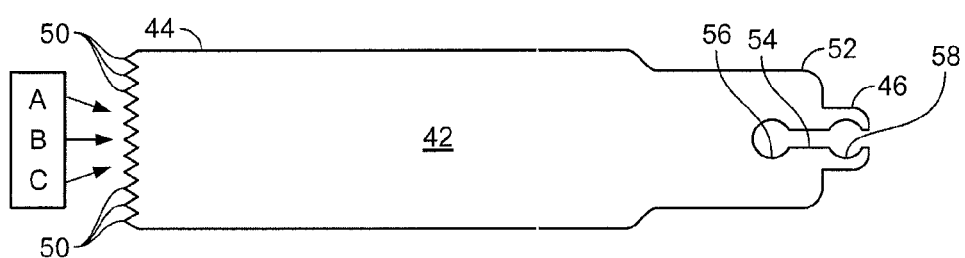
FIG. 7 is a top view of the saw blade of the saw of FIG. 1 marked to show the location of points A, B and C on the blade cutting edge.

A blade path analysis was performed to illustrate possible blade paths for each of points A, B, C on the cutting edge 44 of the blade 42 (FIG. 7). The point B lies on the blade center line. The points A and C are spaced 2 mm from point B on opposed sides thereof, and thus are symmetric with respect to point B.

Possible blade paths are illustrated for a gear ratio of 2:1, and for initial phase angle settings of Φ1=0 degrees and Φ2=N degrees, for each of the points A, B, C along the blade edge. In particular, blade paths are illustrated for N=0 degrees, 22.5 degrees, 45 degrees and 67.5 degrees (FIG. 8), and for N=90 degrees, 112.5 degrees, 135 degrees, and 157.5 degrees (FIG. 9). In these figures, it is assumed that the work piece (e.g. bone) is located at the left side of every plot. In this configuration, a blade path having a generally symmetric figure-eight shape is obtained for point B for initial phase angle settings of Φ1=0 degrees and Φ2=45 degrees (FIG. 8, BIII) and for initial phase angle settings of Φ1=0 degrees and Φ2=135 degrees (FIG. 9, BVII), the symmetry exhibited across both the cutting axis and thrust axis. A blade path having a generally figure-eight shape that is not symmetric about an axis extending in the cutting direction is obtained for point B for phase differences of N=22.5 (FIG. 8, BII), N=157.5 (FIG. 9, BVIII) and others. The blade paths associated with points A and C are generally asymmetric about axes extending in both the cutting direction and in the thrust direction.

Figure 8:
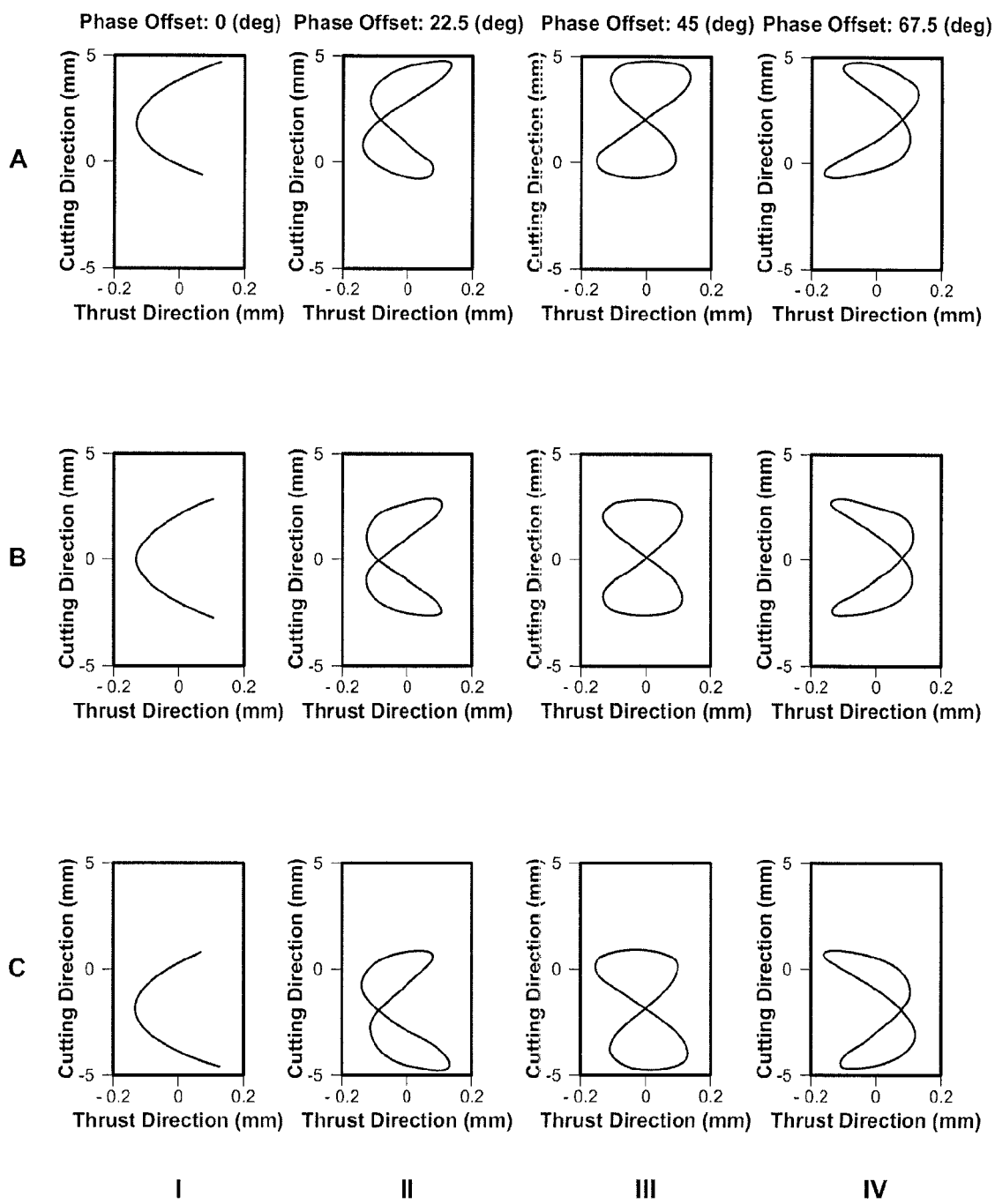
FIG. 8 illustrates the path of travel of the blade cutting edge for a gear ratio of 2:1 for each of the points A, B, and C shown in FIG. 7 for a 0 degree phase offset (column I), a 22.5 degree phase offset (column II), a 45 degree phase offset (column III) and a 67.5 degree phase offset (column IV).
Figure 9:
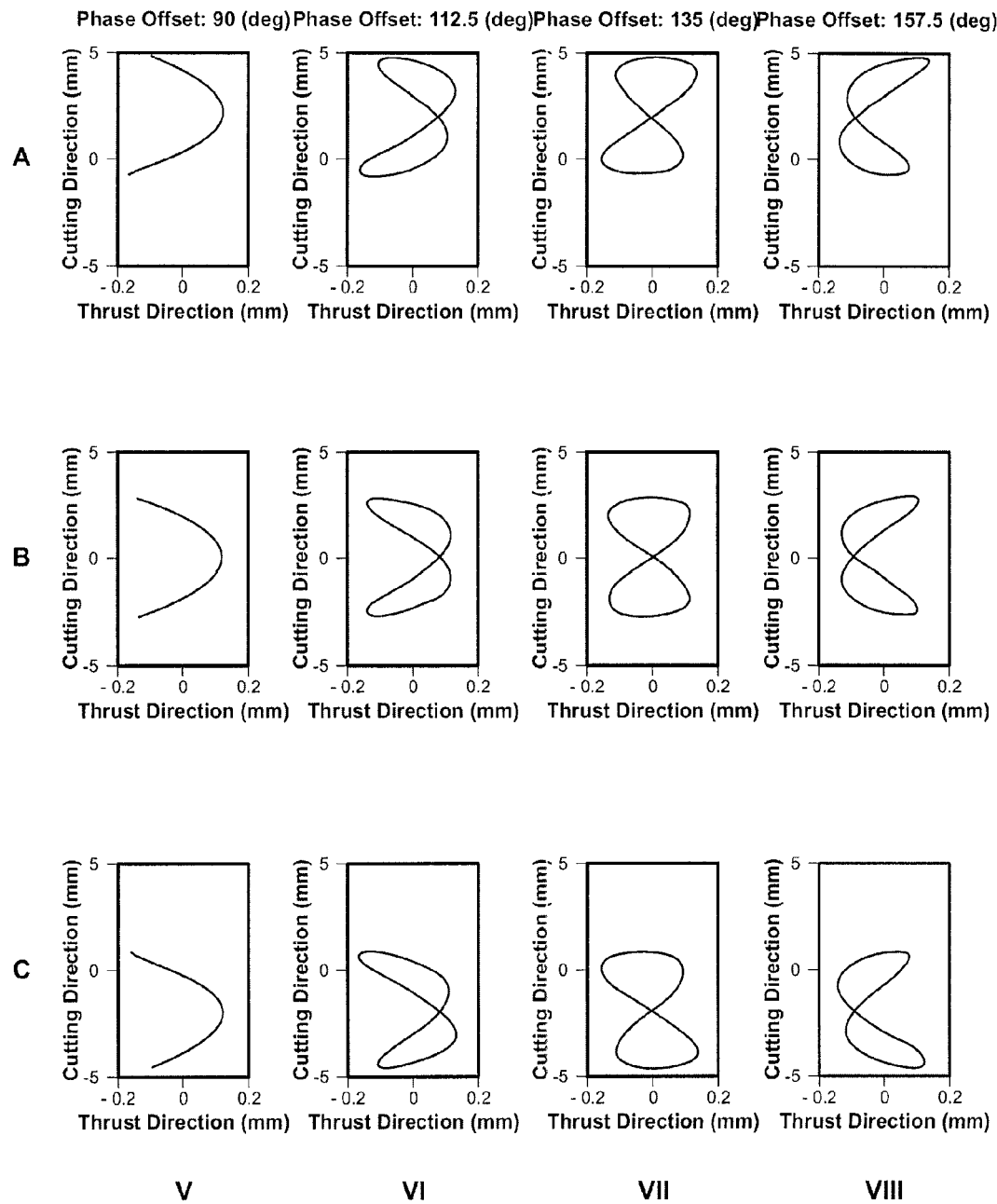
FIG. 9 illustrates the path of travel of the blade cutting edge for a gear ratio of 2:1 for each of the points A, B, and C shown in FIG. 7 for a 90 degree phase offset (column V), a 112.5 degree phase offset (column VI), a 135 degree phase offset (column VII) and a 157.5 degree phase offset (column VIII).

In use, it has been found that a blade path in which the two lobes are more rounded such that the angle of approach is steep (for example as seen in FIG. 8 at location BIV) is less effective for cutting than a blade path in which the two lobes are flattened such that the angle of approach is shallow (for example as seen in FIG. 8 at location BII).

Figure 10:
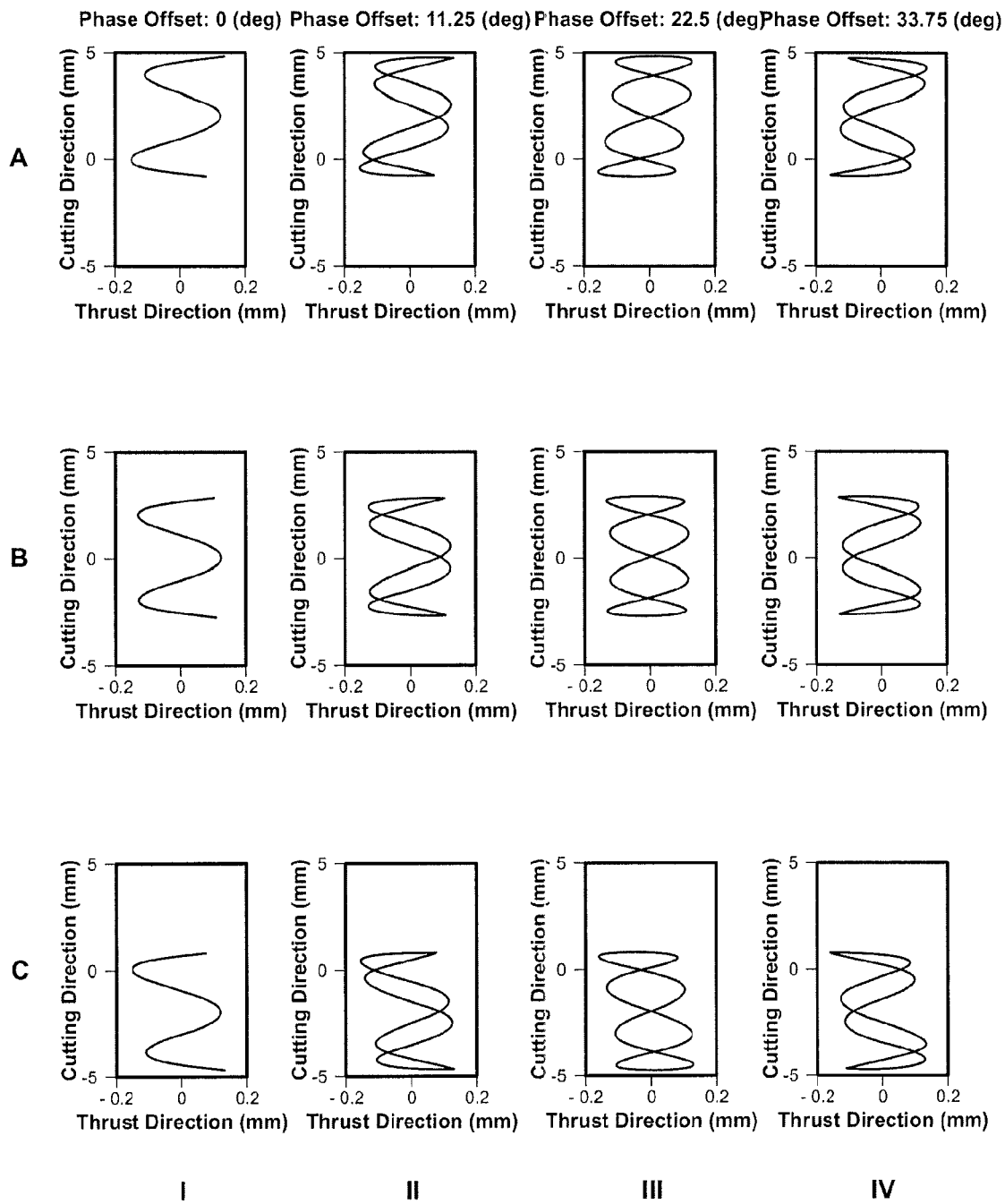
FIG. 10 illustrates the path of travel of the blade cutting edge for a gear ratio of 4:1 for each of the points A, B, and C shown in FIG. 7 for a 0 degree phase offset (column I), a 11.25 degree phase offset (column II), a 22.5 degree phase offset (column III) and a 33.75 degree phase offset (column IV).
Figure 11:
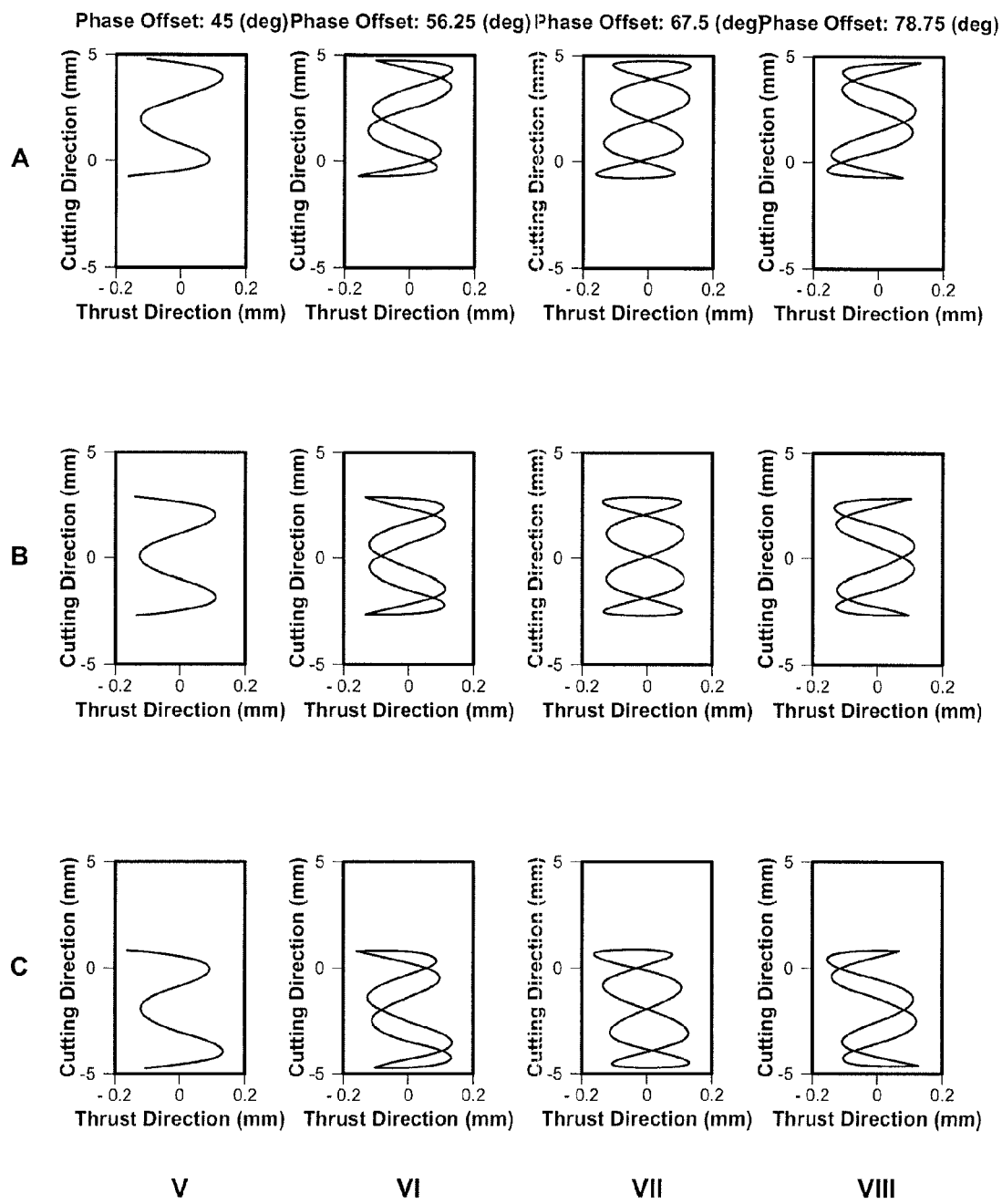
FIG. 11 illustrates the path of travel of the blade cutting edge for a gear ratio of 4:1 for each of the points A, B, and C shown in FIG. 7 for a 45 degree phase offset (column V), a 56.25 degree phase offset (column VI), a 67.5 degree phase offset (column VII) and a 78.75 degree phase offset (column VIII).

Although the gear assembly 100 has been illustrated herein as including gear ratio of the cutting gear 108 and the thrust gear 208 of 2:1, the gear ratio is not limited to this. In some embodiments, the gear assembly may employ gear ratios of greater than 2:1. For example, while the 2:1 gear ratio provides a blade path cycle that is a closed planar loop including two lobes, the loop crossing over itself once, a 3:1 provides a blade path cycle that is a closed planar loop including three lobes, the loop crossing over itself twice. Similarly, a 4:1 gear ratio provides a blade path cycle that is a closed planar loop including four lobes, the loop crossing over itself three times. In each case, the lobes are arranged side by side and adjacent lobes are connected at a node which corresponds to the cross-over location. For gear ratios of 2:1, 3:1, 4:1, . . . , n:1, (n+1):1, a cycle of the blade path is a closed planar loop that crosses over itself at least once during the blade cycle. In particular, for a gear ration of n:1, where n is an integer, a cycle of the blade path is a closed planar loop that crosses over itself (n−1) times during the blade cycle. Referring to FIGS. 10 and 11, possible blade paths are illustrated for a gear ratio of 4:1, and for initial phase angle settings of Φ1=0 degrees and Φ2=N degrees, for each of the points A, B, C along the blade edge. In particular, blade paths are illustrated for N=0 degrees, 11.25 degrees, 22.5 degrees and 33.75 degrees (FIG. 10), and for N=45 degrees, 56.25 degrees, 67.5 degrees, and 78.75 degrees (FIG. 11). In these figures, it is assumed that the work piece (e.g. bone) is located at the left side of every plot. In this configuration, a blade path having a generally symmetric figure-eight shape is obtained for point B for initial phase angle settings of Φ1=0 degrees and Φ2=22.5 degrees (FIG. 10, BIII) and for initial phase angle settings of Φ1=0 degrees and Φ2=67.5 degrees (FIG. 11, BVII), the symmetry exhibited across both the cutting axis and thrust axis. Again, the blade paths associated with points A and C are generally asymmetric about axes extending in both the cutting direction and in the thrust direction.

In the sagittal saw 10, an impulsive thrust loading is implemented to increase the cutting rate. In order to be effective, the impulsive loading is synchronized with the cutting motion of the blade. In particular, the saw 10 is configured so that the impulsive loading is an integer multiple of the frequency of the blade cycle. In the illustrated embodiment, the saw 10 is configured so that the impulsive loading is twice the frequency of the blade cycle, such that it forces the blade into the bone surface at the start of each stroke, and pulls the blade from the surface at the end of each stroke. The embodiment illustrated here has been shown to produce cutting rates that are significantly higher than some conventional sagittal saws employing an arc-shaped blade path or an elliptical blade path.

Although the sagittal saw 10 is described as including a motor-driven gear assembly configured to provide the desired blade path, the sagittal saw 10 is not limited to using this drive system. For example, in other embodiments, the gear assembly may be replaced with electro-mechanical or pneumatic devices configured to provide the desired blade path.

Although the sagittal saw 10 is illustrated herein as a cordless saw including a rechargeable battery pack, the sagittal saw 10 may be powered externally. For example, the motor 22 may be powered via a power cord configured to be connected to a conventional AC power source, or may be located externally.

A selected illustrative embodiment of the invention is described above in some detail. It should be understood that only structures considered necessary for clarifying the present invention have been described herein. Other conventional structures, and those of ancillary and auxiliary components of the system, are assumed to be known and understood by those skilled in the art. Moreover, while a working example of the present invention has been described above, the present invention is not limited to the working example described above, but various design alterations may be carried out without departing from the present invention as set forth in the claims.

What is claimed is:
1. A cutting device comprising:
a blade including a first end, a second end opposed to the first end, and a longitudinal axis extending between the first end and second end, the first end extending transverse to the longitudinal axis, movement of the first end defining a blade path; and
an actuator connected to the blade second end, the actuator configured to drive the blade so that the blade path comprises a cyclic closed planer loop that crosses over itself at least once per blade path cycle;
wherein the actuator comprises a gear assembly configured to be driven by a motor, the gear assembly; including;
a thrust shaft driven by the motor, the thrust shaft including an end and a thrust crank protruding from the thrust shaft end so as to extend parallel to and spaced apart from an axial centerline of the thrust shaft,
a first gear mounted on the thrust shaft,
a cutting shaft parallel to the thrust shaft, the cutting shaft including an end and a cutting crank protruding from the cutting shaft end so as to extend parallel to and spaced apart from an axial centerline of the cutting shaft, a second gear mounted on the cutting shaft and driven by the first gear, and a pivot shaft parallel to the cutting shaft, wherein the first and second gears are dimensioned so that the rotational speed of the thrust shaft is greater than the rotational speed of the cutting shaft.

2. The cutting device of claim 1 wherein in one blade path cycle, the blade path comprises a closed plane loop consisting of at least two lobes meeting at a node.

3. The cutting device of claim 2 wherein the lobes are symmetric.

4. The cutting device of claim 2 wherein the lobes are asymmetric.

5. The cutting device of claim 1 wherein the blade path is symmetric about an axis parallel to the longitudinal axis.

6. The cutting device of claim 1 wherein a portion of the blade path corresponding to a first reciprocation of the at least two reciprocations is a different portion than a portion of the blade path corresponding to a second reciprocation of the at least two reciprocations.

7. The cutting device of claim 1 wherein the blade moves along the blade path in such a way that a workpiece is cut both in a first direction and a second direction, the second direction being opposed to the first direction.

8. The cutting device of claim 7 wherein the first direction and second direction are generally transverse to the blade longitudinal axis.

9. The cutting device of claim 7 wherein the movement in the second direction is subsequent to movement in the first direction.

10. The cutting device of claim 7 wherein the blade cuts the work piece in both the first direction and a second direction within the same blade path cycle.

11. The cutting device of claim 1 wherein in one blade path cycle, the blade moves along the blade path in such a way that a work piece is cut both in a first direction and a second direction, the second direction being opposed to the first direction, wherein the portion of the blade path corresponding to movement in the first direction is a different portion than the portion of the blade path corresponding to movement in the second direction.

12. The cutting device of claim 1 wherein the first and second gears are dimensioned so that the rotational speed of the thrust shaft is an integer multiple of the rotational speed of the cutting shaft.

13. The cutting device of claim 1 wherein the first and second gears are dimensioned so that the rotational speed of the thrust shaft is at least twice the rotational speed of the cutting shaft.

14. The cutting device of claim 1, wherein
the cutting crank is connected to the blade using a first guide configured to convert the rotary motion of the cutting crank to a linear motion of the blade that is transverse to the longitudinal axis,
the thrust crank is connected to the blade at a location between the first guide and the first end using a second guide, the second guide configured to convert the rotary motion of the thrust crank to a linear motion of the blade that is parallel to the longitudinal axis, and
the pivot shaft is connected to the blade at a location between the second guide and the first end using a third guide, the third guide configured to constrain the longitudinal axis of the blade to intersect with a longitudinal axis of the pivot shaft.

15. The cutting device of claim 14 wherein the first guide, second guide and third guide are linear guide bearings.

16. The cutting device of claim 1 wherein the cutting crank and the thrust crank are arranged so that an initial phase difference exists between the cutting crank angular position and the thrust crank angular position.

17. The cutting device of claim 16 wherein the cutting crank and the thrust crank are arranged so that the initial phase difference between the cutting crank angular position and the thrust crank angular position is greater than 0 degrees and less than 90 degrees.

18. The cutting device of claim 16 wherein the cutting crank and the thrust crank are arranged so that the initial phase difference between the cutting crank angular position and the thrust crank angular position is greater than 90 degrees and less than 180 degrees.

19. A cutting device comprising:
a blade including a first end, a second end opposed to the first end, and a longitudinal axis extending between the first end and second end, the first end extending transverse to the longitudinal axis, movement of the first end defining a blade path; and
an actuator connected to the blade second end, the actuator configured to drive the blade so that the blade path is cyclic and includes at least two reciprocations parallel to the longitudinal axis for each blade path cycle, wherein the actuator comprises a gear assembly configured to be driven by a motor, the gear assembly including:
a thrust shaft driven by the motor, the thrust shaft including an end and a thrust crank protruding from the thrust shaft end so as to extend parallel to and spaced apart from an axial centerline of the thrust shaft, including
a first gear mounted on the thrust shaft,
a cutting shaft parallel to the thrust shaft, the cutting shaft including an end and a cutting crank protruding from the cutting shaft end so as to extend parallel to and spaced apart from an axial centerline of the cutting shaft,
a second gear mounted on the cutting shaft and driven by the first gear, and
a pivot shaft parallel to the cutting shaft, wherein the first and second gears are dimensioned so that the rotational speed of the thrust shaft is greater than the rotational speed of the cutting shaft.

20. The cutting device of claim 19, wherein the blade path crosses over itself at least once per blade cycle.

21. The cutting device of claim 19, wherein in one blade path cycle, the blade path comprises a closed plane loop consisting of at least two lobes meeting at a node.

22. The cutting device of claim 21 wherein the lobes are symmetric.

23. The cutting device of claim 21 wherein the lobes are asymmetric.

24. The cutting device of claim 19 wherein the blade path is symmetric about an axis parallel to the longitudinal axis.

25. The cutting device of claim 19 wherein the portion of the blade path corresponding to a first reciprocation of the at least two reciprocations is a different portion than the portion of the blade path corresponding to a second reciprocation of the at least two reciprocations.

26. The cutting device of claim 19 wherein the blade moves along the blade path in such a way that a workpiece is cut both in a first direction and a second direction, the second direction being opposed to the first direction.

27. The cutting device of claim 19 wherein in one cycle of the blade path, the blade moves along the blade path in such a way that a work piece is cut both in a first direction and a second direction, the second direction being opposed to the first direction, wherein the portion of the blade path corresponding to movement in the first direction is a different portion than the portion of the blade path corresponding to movement in the second direction.

28. The cutting device of claim 27 wherein the first direction and second direction are generally transverse to the blade longitudinal axis.

29. The cutting device of claim 27 wherein the movement in the second direction is subsequent to movement in the first direction.

30. The cutting device of claim 19 wherein the first and second gears are dimensioned so that the rotational speed of the thrust shaft is an integer multiple of the rotational speed of the cutting shaft.

31. The cutting device of claim 19 wherein the first and second gears are dimensioned so that the rotational speed of the thrust shaft is twice the rotational speed of the cutting shaft.

32. The cutting device of claim 19 wherein
the cutting crank is connected to the blade using a first guide configured to convert the rotary motion of the cutting crank to a linear motion of the blade that is transverse to the longitudinal axis,
the thrust crank is connected to the blade at a location between the first guide and the first end using a second guide, the second guide configured to convert the rotary motion of the thrust crank to a linear motion of the blade that is parallel to the longitudinal axis, and
the pivot shaft is connected to the blade at a location between the second guide and the first end using a third guide, the third guide configured to constrain the longitudinal axis of the blade to intersect with a longitudinal axis of the pivot shaft.

33. The cutting device of claim 32 wherein the first guide, second guide and third guide are linear guide bearings.

34. The cutting device of claim 19 wherein the cutting crank and the thrust crank are arranged so that an initial phase difference exists between the cutting crank angular position and the thrust crank angular position.

35. The cutting device of claim 34 wherein the cutting crank and the thrust crank are arranged so that the initial phase difference between the cutting crank angular position and the thrust crank angular position is greater than 0 degrees and less than 90 degrees.

36. The cutting device of claim 34 wherein the cutting crank and the thrust crank are arranged so that the initial phase difference between the cutting crank angular position and the thrust crank angular position is greater than 90 degrees and less than 180 degrees.

* * * * *